(12) United States Patent
Bouvier

(10) Patent No.: US 6,177,954 B1
(45) Date of Patent: Jan. 23, 2001

(54) MINIATURE INSPECTION SYSTEM

(75) Inventor: William P. Bouvier, New Boston, NH (US)

(73) Assignee: Northeast Robotics LLC, Weare, NH (US)

(*) Notice: Under 35 U.S.C. 154(b), the term of this patent shall be extended for 0 days.

(21) Appl. No.: 09/087,239

(22) Filed: May 29, 1998

(51) Int. Cl.[7] .............................. H04N 7/18; H04N 9/47
(52) U.S. Cl. ................................... 348/92; 348/95
(58) Field of Search ....................... 348/86–96; 356/394, 356/397; H04N 7/18, 9/47

(56) References Cited

U.S. PATENT DOCUMENTS

| | | | |
|---|---|---|---|
| 4,618,938 | * 10/1986 | Sandland et al. | 364/552 |
| 5,386,293 | * 1/1995 | Barnard et al. | 356/397 |
| 5,420,689 | * 5/1995 | Siu | 356/394 |
| 5,623,303 | * 4/1997 | Inoue et al. | 348/96 |
| 5,867,741 | * 2/1999 | Maruyama et al. | 396/187 |
| 5,877,494 | * 3/1999 | Larsen et al. | 250/234 |

* cited by examiner

Primary Examiner—Howard Britton
Assistant Examiner—Nhon T Diep
(74) Attorney, Agent, or Firm—Davis and Bujold

(57) ABSTRACT

A miniature inspection system for observing an object. The system comprises a camera defining an optical axis defined between the camera and the object when located at an inspection location. A ring light is located concentrically with respect to and along the optical axis at a location between an entrance aperture of the camera and the inspection location. A field lens is located along the optical axis at a location between the camera and the ring lights. A mirror or a penta-prism may be located along the optical axis, between the camera and the field lens, so that light reflected from the object along the optical axis is reflected by either the mirror or the penta-prism toward the entrance aperture of the camera. An illumination source, may be also provided to supply illumination along the optical axis of the system.

19 Claims, 1 Drawing Sheet

MINIATURE INSPECTION SYSTEM

The present invention relates to a mounted camera used in conjunction with an illumination source having a diffuser associated therewith, a reflective surface, and a field lens, to provide a compact inspection system which is extremely small in size and facilitates use within the small confines of semiconductor processing equipment.

BACKGROUND OF THE INVENTION

There are a variety of known inspection systems which illuminate a flat surface to be inspected such as a laser-etched art work semiconductor lead framework. However, most of the known inspection systems are of a relatively large size which do not easily fit within the small confines of currently available semiconductor processing equipment.

In particular, known arrangements typically affix a ring of LEDs to the underside of rather large and bulky inspection equipment. The ring of LEDs is centered about the optical axis which extends normal to the inspection surface. This illumination geometry is useful for imaging "mirror melting" by a laser of desired art work on a diffusely reflecting metal surface. In the area affected by the laser, the diffused surface finish is melted to convert that surface area into a highly specular surface finish. This specular surface finish reflects the low-angle dark field illumination off at an equivalent low-angle causing it to appear dark in the field of view. The diffuse background finish reflects some of the incident low-angle illumination along the optical axis into the camera lens and hence that area appears bright. This combination causes the "mirror melting" laser mark to appear in high contrast, e.g. black on a white surface, rendering it fairly easy to decipher by conventional machine vision systems.

If the lead frame surface finish is highly specular, however, the dark field illumination geometry described above will cause the surface to appear black, hence rendering invisible any "mirror melting" art work, e.g. a dark field on a dark field. On such a highly specular surface for laser etching to be visible under a dark field illumination the surface must be optically "roughed up" by the laser. For example, the surface must be etched so as to form small craters or pits. Under dark field illumination, only the rim of the laser pits will reflect light to the camera while the valleys of the pits will reflect the light to the surrounding environment. If the pits are small enough and spaced closely enough together they can be made to appear as a "solid" feature. If the pits are isolated and enlarged, however, they appear as bright rings on a dark background, potentially causing problems with the inspection algorithms currently used in prior art systems.

SUMMARY OF THE INVENTION

Wherefore, it is an object of the present invention to overcome the aforementioned problems and drawbacks associated with the prior art designs.

The present invention relates to an miniature inspection system for observing an object, where the inspection system has a camera, an illumination source associated with a diffuser, a field lens and a penta-prism. The inspection systems provides bright field illumination to a desired surface.

Additionally, the illumination source provides for diffused illumination of the object to be observed. In applications where the marks on the object being observed are relatively small, the illumination source does not have to be significantly larger in size than the camera aperture itself.

The term "diffuse", as used in this specification and the appended claims, means a light source which is dispersed over a broad range of incident angle of azimuth and elevation with respect to the object being observed, and the light source approaches complete coverage over the area where the light is directed, i.e. greater than 25% of the possible angular range of incident light. The term "concealed", as used in this specification and appended claims, when referring to the diffuser and the object to be inspected, means that the surface emitting the diffused light from the diffuser is positioned such that the emitting surface of the diffuser can not directly illuminate the object, i.e. only indirect illumination of the object by reflection of light off the beam splitter or the side wall(s) of the housing or supplying light through the beam splitter can occur.

Further objects and advantages of the present invention are apparent from the following description and disclosure, references being made to the drawings setting forth features of the present invention in greater detail.

BRIEF DESCRIPTION OF THE DRAWINGS

The invention will now be described, by way of example, with reference to the accompanying drawings in which.

DESCRIPTION OF THE PREFERRED EMBODIMENT(S)

Figure 1:
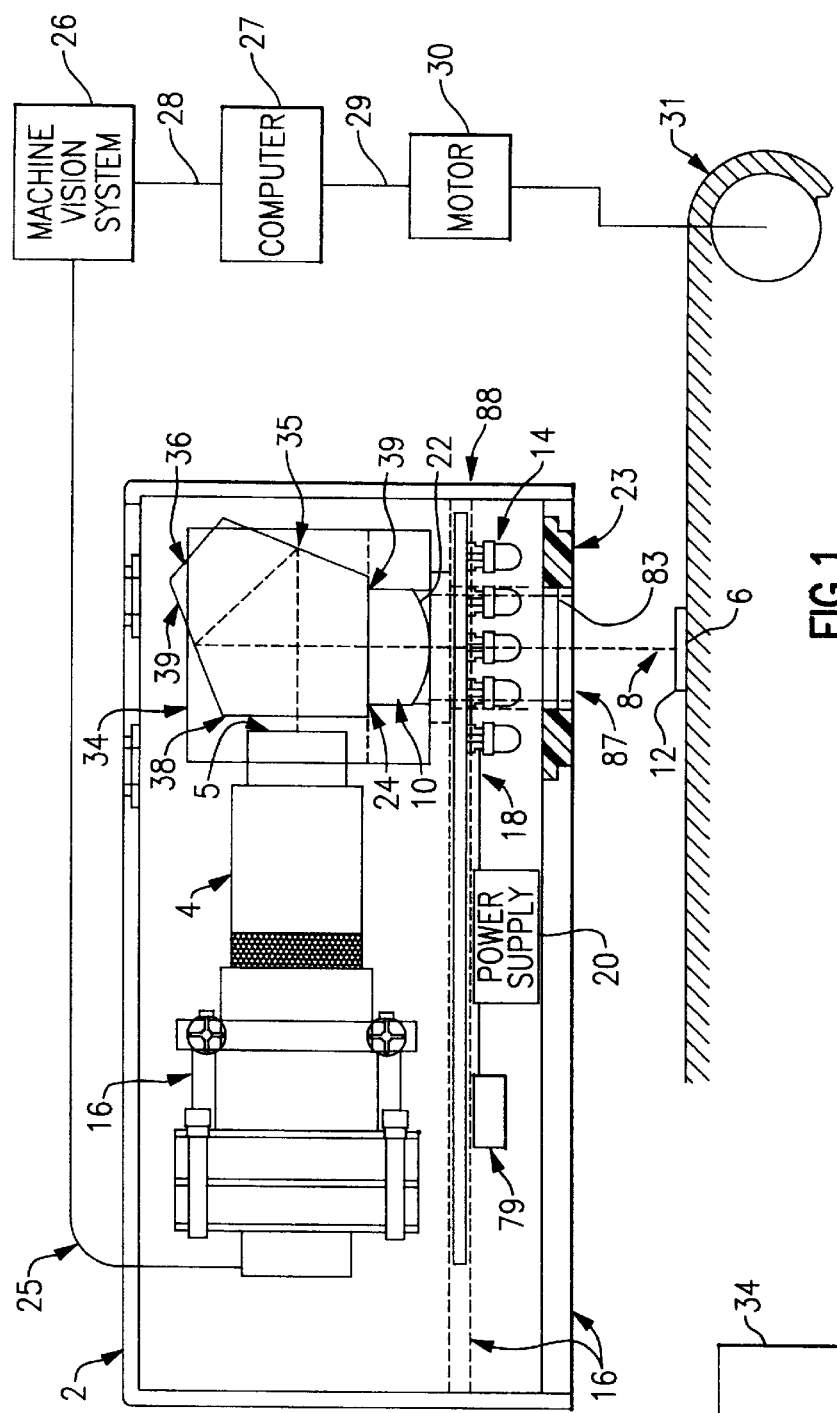
FIG. 1 is a diagrammatic representation of an embodiment of the inspection system according to the present invention.

With reference to FIG. 1, an embodiment of the present invention will now be described in detail. As can be seen is FIG. 1, the inspection system generally comprises a board-level miniature video camera 4, such as a CCD (charge coupled device) camera, a CMOS (metal oxide semiconductor) camera or some other observation or inspection device which is well known in the art. The camera 4 is positioned for viewing an object 6 to be inspected and an optical axis 8 is defined between the camera 4 and the object 6. A field lens 10 is positioned along the optical axis 8, at a location between a camera lens entrance aperture 5 and an inspection surface 12 of the object 6. It is to be appreciated that the field lens 10 is supported within the system 2 in a conventional manner (not shown in specific detail) such that the field lens 10 can be readily interchanged or replaced with a variety of other field lens, having different focusing characteristics, so that by selecting an appropriate power of the field lens a wide range of optical magnifications and/or fields of view can be achieved by the system 2.

The interchangeable or replaceable field lens feature provides additional flexibility to the basic design of the present invention.

Additionally, a penta-prism 34 is located along the optical axis 8 between the camera 4 and the field lens 10 to alter the path of the optical axis 8. The penta-prism 34 is supported conventionally within the system 2 in the same manner as the field lens 10. The penta-prism 34 has five surfaces 35, 36, 37, 38 and 39. Only two of these surfaces are utilized for reflecting light, e.g. the first and second reflective surfaces 35 and 37, respectively, while two other surfaces are utilized for transmitting light, e.g. the first and second transmissive surfaces 38 and 39, respectively. The first reflective surface 35 is disposed at approximately 67.5° with respect to the optical axis 8 of the camera 4 while the second reflective surface 37 is disclosed at approximately 22.5° with respect to the optical axis 8 of the camera 4. The first and second transmissive surfaces 38 and 39 both lie substantially normal, e.g. lie at an angle of about 900, respectively, with respect to the optical axis 8.

A ring of LEDs 14 is affixed internally to the system 2, e.g. to the interior of a conventional framework 16 of the system, and the optical axis 8 extends through the center of the ring of LEDs 14. The ring of LEDs 14 is powered, via electrical wiring 18, by an appropriate power source 20 and the power is controlled by a rheostat 79 to facilitate desired illumination of the top surface of the object 6 to be inspected by the ring of LEDs 14 at different light intensities. A ring diffuser 23 is affixed to the underside of the conventional framework of the system and located between the ring of LEDs 14 and the top surface of the object 6 to be inspected such that the optical axis 8 additionally extends through the center of the ring diffuser 23.

During use, the light from the LEDs 14 is supplied through the diffuser 23 toward the object 6 to be inspected. Some of the light supplied by the ring of LEDs 14 through the diffuser 23 is reflected by the surface 12 of the object 6 to be inspected to the surrounding environment. The remaining light, supplied by the ring of LEDs 14, through the diffuser 23, is reflected off the surface 12 of the object 6 along the optical axis 8 toward the field lens 10.

The light enters a first surface 22 of the field lens 10 and is altered by the internal focusing characteristics of the field lens 10. The focused light exits the rear surface 24 of the field lens 10 and then is supplied to and enters the second transmissive surface 39 of the penta-prism 34, which is arranged substantially normal to the optical axis 8, so the light passes substantially directly therethrough and is substantially unaltered by the second transmissive surface 39. The light then is reflected off the second reflective surface 37 of penta-prism 34 toward the first reflective surface 35 of the penta-prism 34. The light then reflects off the first reflective surface 35 of the penta-prism and exits through the first transmissive surface 38 of the penta-prism and is supplied toward the lens entrance aperture 5 of the camera 4. The focused light finally enters the camera 4, via the lens entrance aperture 5, and is appropriately sensed by the internal sensing mechanism of the camera 4. Since the internal sensing feature of camera 4 is well known to those skilled in this art, a further detailed description concerning the same is not provided herein.

The camera 4 is, in turn, coupled to a machine vision system 26 (only diagrammatically shown), via a conventional cable 25, for determining the sensed image, e.g. by a comparison of the sensed image with prior input features, images, characters, objects, contours, shapes, indicia, etc. Once the desired characteristic, feature, etc., of the object(s) 6 to be observed or inspected is determined by the system 2, the object(s) 6 can then be further manipulated by the system, e.g. the object can be accepted or rejected, can be package or further conveyed, can be sorted by size, shape, or type, etc., depending upon the particular application. The machine vision system 26, in turn, is connected to a computer 27 via a conventional cable 28. The computer 27 is typically electrically connected, by a cable 29, to a motor 30 which rives a conveyor 31 or some other transportation or conveying device for controlling further manipulation or manufacturing of the object 6, e.g. for inspection, transportation, processing, sorting orientation, etc. As the present invention primarily relates to the inspection system 2, a further detailed description concerning the machine vision system 26 and its associated components will not be provided.

It is to be appreciated that the penta-prism 34 is interchangeable with a pair of flat mirrors which may be disposed at angles of approximately 67.5° and 22.5° with respect to the optical axis 8 of the camera 4, or other combinations of angles which have the effect of redirecting the optical axis of the camera at approximately a right angle for viewing the surface 12 to be inspected. The purpose of the penta-prism or the pair of flat mirror surfaces is to twice invert the image of the object to be inspected so it is perceived by the camera 4 in a right side up fashion rather than in an inverted fashion.

In the disclosed embodiment of the present invention, the system is preferably contained within a small exterior system housing 88. The system housing 88 has a height dimension of no more than about 3¼ inches, and preferably a height of between 1.5 and 2.0 inches, a width dimension of about 1.5 inches, preferably a width dimension of between 1.25 and 1.75 inches, and a depth dimension of about 5 inches, and preferably a depth of between 4.5 and 5.5 inches. The miniaturization or small size of the system housing 88, according to the present invention, facilitates placement of the system within the small confines of conventional semiconductor processing equipment.

The system housing 88 has at least one aperture 87 provided in a base surface thereof and all of the components which define or alter the optical axis 8 of the system 2 are arranged with in the system housing 88 so that the optical axis 8 extends through the at least one aperture 87 of the system housing. The ring light, or some other known or conventional illumination source, is affixed adjacent the at least one aperture 87, and provided for supplying illumination at an angle with respect to the optical axis.

Figure 2:
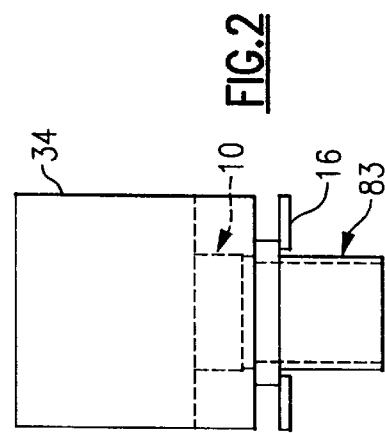
FIG. 2 is a diagrammatic representation of a cylindrical shield or ferrule according to the present invention.

A cylindrical shield or ferrule 83 (FIG. 2) is secured to and extending from the base of the framework 16. The ferrule 83 serves a number of functions. First, the ferrule 83 is preferably painted black on the inside to prevent "blow-back" of light from any LED of the ring of LEDs 14 back to the penta-prism and/or the camera lens, i.e. to absorb light supplied directly by any one of the LEDs. Second, the ferrule 83 is painted white on the outside to help disperse and diffuse light within the LED ring circuit chamber of the ring of LEDs 14. Third, the ferrule 83 helps position the optical axis 8 properly with respect to the LED circuit. That is, the base of the housing 88 has at least one circular hole or aperture 87 provided therein and the ferrule 83 is the same size or slightly larger in size than the at least one aperture 87.

In a preferred form of the invention, the camera is a "board-level" camera which is particularly small in size. The small size of the camera is crucial to the utility and the function of the imaging module according to the present invention.

It is to be appreciated that a penta-prism 34 is preferred over a pair of mirror as any slight misalignment of the penta-prism 34, within a mounting slot, will still facilitate an accurate reflection of the light from the object at an angle of 90°. Secondly, the penta-prism is easy to clean because both transmissive surfaces are exposed (face outwardly) while, if two separate mirrors are employed, the reflective surfaces of the two separate mirrors face inwardly and are much more difficult to maintain in a clean condition. Lastly, the machining of the mounting member(s) for supporting the penta-prism is simpler than manufacturing a mounting arrangement for mounting two separate mirrors, e.g. cylindrical bores and right-angle cuts are required rather than narrow slots at odd angles.

In a preferred form of the invention, the penta-prism 34 and the field lens 10 are glued in place with optical UV-cured epoxy rather than by being fastened to the housing via mounting screws and/or retaining rings. Such attachment simplifies the machining of the apparatus and reduces the number of components thereby further minimizing the chances of damaging the optical components during assembly or at the inspection site.

Preferably, the field lens is an off-the-shelf 25 mm "lipstick" lens. It is to be appreciated, however, that the use of 50 mm achromat field lens also allow a desired field of view (4.5 mm×6.00 mm) to be achieved at the required distance dictated by the penta-prism and the light source dimensions. However, the inventor has determined that placing the field lens between the camera lens and the penta-prism, rather than placing the field lens between the penta-prism and the object, generally does not provide satisfactory optical results.

Since certain changes may be made in the above described observation system, without departing from the spirit and scope of the invention herein involved, it is intended that all of the subject matter of the above description or shown in the accompanying drawing shall be interpreted merely as examples illustrating the inventive concept herein and shall not be construed as limiting the invention.

I claim:

1. A miniature inspection system for observing an object, the inspection system comprising:
   a camera for inspecting an object when located at an inspection location, the camera having an entrance aperture lense and an optical axis being defined between the entrance aperture lense of the camera and the inspection location;
   a ring light, for providing light to the object to be inspected, being located concentrically with respect to and along the optical axis, at a location between the entrance aperture lense of the camera and the inspection location;
   a field lens being located along the optical axis at a location between the entrance aperture lense of the camera and the inspection location;
   at least one reflective surface being located along the optical axis, between the entrance aperture lense of the camera and the field lens; and
   a diffuser being located between the ring light and the inspection location to diffuse the light supplied by the ring light to the object when located at an inspection location.

2. The miniature inspection system according to claim 1, wherein said at least one reflective surface is a penta-prism.

3. The miniature inspection system according to claim 1, wherein the ring light is a planar ring light and contains a plurality of LEDs, and said plurality of LEDs are aligned with the diffuser to provide diffused illumination of the object to be inspected.

4. The miniature inspection system according to claim 1, wherein the ring light is powered by a power source which has a mechanism for controlling an the intensity and character of the light supplied by the ring light for providing illumination.

5. The miniature inspection system according to claim 1, in combination with a vision system which is electrically coupled to said miniature inspection system, a computing mechanism which is electrically coupled to said vision system, and a conveying mechanism which is electrically coupled to said computing mechanism, and said vision system supplies a sensed image of the object to be inspected to said computing mechanism which determines one of a characteristic and a feature of said object and outputs a signal to said conveying mechanism to control further manipulation of said object in view of one of said characteristic and feature.

6. The miniature inspection system according to claim 1, wherein the camera is a board-level camera.

7. The miniature inspection system according to claim 1, wherein the field lens 50 mm is an achromat field lens.

8. The miniature inspection system according to claim 1, wherein the inspection system includes a system housing which has a height dimension of no greater than about 3½ inches, a width dimension of about 1.5 inches, and a depth dimension of about 5 inches.

9. The miniature inspection system according to claim 1, wherein the inspection system includes a ferrule which is centered with respect to the optical axis, the ferrule extends alone the optical axis and is locate between the ring light and the optical axis to separate the ring light from the optical axis, and an inwardly facing surface of the ferrule being black to function as a light trap and absorb any stray light from the ring light.

10. The miniature inspection system according to claim 9, wherein the ferrule is white on an outside thereof to disperse and diffuse light from the ring light.

11. A miniature inspection system for observing an object, the inspection system comprising:
    a housing having an observation aperture therein;
    a camera, located within the housing, for inspecting an object when located at an inspection location, and an optical axis being defined between a lense of the camera and the inspection location and extending through the aperture in the housing;
    a surrounding light, supported by the housing, for providing light to the object to be inspected, the surrounding light being located concentrically with respect to and along the optical axis, at a location between an entrance aperture of the camera and the inspection location;
    a field lens, located within the housing, being located along the optical axis at a location between the lense of the camera and the inspection location;
    at least one reflective surface, located within the housing, being located along the optical axis, between lense of the camera and the field lens;
    a ferrule, supported by the housing, extending along the optical axis, the ferrule defining the observation aperture of the housing and, the ferrule being locate between the surrounding light and the optical axis to separate the surrounding light from the optical axis, and an inwardly facing surface of the ferrule being black to function as a light trap and absorb any stray light from the surrounding light; and
    a diffuser, supported by the housing, being located between the surrounding light and the inspection location to diffuse the light supplied by the surrounding light to the object when located at the inspection location.

12. The miniature inspection system according to claim 11, wherein said at least one reflective surface is formed by a penta-prism.

13. The miniature inspection system according to claim 11, wherein the surrounding light is a planar surrounding light and contains a plurality of LEDs, and said plurality of LEDs are aligned with the diffuser to provide diffused illumination of the object to be inspected.

14. The miniature inspection system according to claim 11, wherein the surrounding light is powered by a power source which has a mechanism for controlling both an intensity and character of the light supplied by the surrounding light for providing illumination.

15. The miniature inspection system according to claim 11, in combination with a vision system which is electrically coupled to said miniature inspection system, a computing mechanism which is electrically coupled to said vision system, and a conveying mechanism which is electrically coupled to said computing mechanism, and said vision system supplies a sensed image of the object to be inspected to said computing mechanism which determines one of a characteristic and a feature of said object and outputs a signal to said conveying mechanism to control further manipulation of said object in view of one of said characteristic and feature.

16. The miniature inspection system according to claim 11, wherein the camera is a board-level camera.

17. The miniature inspection system according to claim 11, wherein the field lens 50 mm is an achromat field lens.

18. The miniature inspection system according to claim 11, wherein the inspection system includes a system housing which has a height dimension of no greater than about 3¼ inches, a width dimension of about 1.5 inches, and a depth dimension of about 5 inches.

19. A miniature inspection system for observing an object, the inspection system comprising:

a housing having an observation aperture therein, the housing accommodating;

a board level camera, having a lense, for inspecting an object when located at an inspection location, and an optical axis being defined between the board level camera and the inspection location and extending through the aperture in the housing;

a surrounding light, for providing light to the object to be inspected, being located concentrically with respect to and along the optical axis, at a location between an entrance aperture of the board level camera and the inspection location;

a field lens being located along the optical axis at a location between the board level camera and the surrounding light;

a penta-prism being located along the optical axis, between the board level camera and the field lens, for reflecting light supplied by the field lens toward the board level camera;

a ferrule being located adjacent the observation aperture of the housing and extending along the optical axis, the ferrule being locate between the surrounding light and the optical axis to separate the surrounding light from the optical axis, and an inwardly facing surface of the ferrule being black to function as a light trap and absorb any stray light from the surrounding light and an outwardly facing surface of the ferrule being white to disperse and diffuse light supplied by the surrounding light; and a diffuser being located between the surrounding light and the inspection location to diffuse the light supplied by the surrounding light to the object when located at the inspection location.

* * * * *